United States Patent [19]

Palla et al.

[11] 4,301,174

[45] Nov. 17, 1981

[54] FUNGICIDAL N-ACYL-S-HALOALKYL (OR S-HALOVINYL) THIOLCARBAMATES AND PROCESS FOR PREPARING SAME

[75] Inventors: Ottorino Palla, Crema; Remo Galli, Dresano; Franco Gozzo, San Donato Milanese; Simone Lorusso, San Giuliano Milanese, all of Italy

[73] Assignee: Montedison S.p.A., Milan, Italy

[21] Appl. No.: 178,594

[22] Filed: Aug. 15, 1980

[30] Foreign Application Priority Data

Aug. 16, 1979 [IT]  Italy ............................... 25144 A/79
Oct. 9, 1979 [IT]  Italy ............................... 26341 A/79

[51] Int. Cl.³ .................... A01N 47/10; C07C 155/02
[52] U.S. Cl. ............................ 424/300; 260/455 A
[58] Field of Search ................... 260/455 A; 424/300

[56] References Cited

U.S. PATENT DOCUMENTS

| 2,977,209 | 3/1961 | Tilles et al. | 260/455 A |
|---|---|---|---|
| 3,265,563 | 8/1966 | Tilles et al. | 260/455 A |
| 3,845,091 | 10/1974 | Singer | 260/455 A |
| 4,056,549 | 11/1977 | Rinehart | 260/455 A |

*Primary Examiner*—Henry R. Jiles
*Assistant Examiner*—Robert C. Whittenbaugh

[57] ABSTRACT

New, highly active fungicides which are N-acyl-S-haloalkyl, or S-halovinyl-thiolcarbamates are prepared by reacting a carboxylic acid, e.g., benzoic acid, with an imidoyl chloride, such as trichloromethylthiomidoyl chloride. These new fungicide thiolcarbamates are effective in fighting a wide range of fungi which attack useful plants, being particularly active against fungi belonging to the different orders Ficomicoeti, Ascomicoeti and Basidiomicoeti.

23 Claims, No Drawings

FUNGICIDAL N-ACYL-S-HALOALKYL (OR S-HALOVINYL) THIOLCARBAMATES AND PROCESS FOR PREPARING SAME

BACKGROUND OF THE INVENTION

S-substituted phenyl N-alkyl-thiolcarbamates which are described as active against the specific fungus, Pythium ultimum, are disclosed in U.S. Pat. No. 4,056,549. Certain other thiolcarbamates have been described as effective against various plant pests, and as being herbicides, insecticides, miticides, etc. U.S. Pat. No. 3,265,563 describes S-phenyl N-alkylthiolcarbamates, S-chlorophenyl N-alkylthiolcarbamates, S-ethoxyphenyl N-allylthiolcarbamates, S-ethoxyphenyl-N-alkylthiolcarbamates, S-p-tolyl N-alkylthiolcarbamates, and S-2,4-dimethylphenyl N-alkylthiolcarbamates as herbicides and fungicides.

THE PRESENT INVENTION

One object of this invention is to provide new fungicides which are highly active against different orders of fungi which infest useful plants and in particular fungi belonging to the different orders of Ficomicoeti, Ascomicoeti and Basidimicoeti.

Another object is to provide a process for preparing the highly active, versatile fungicides.

These and other objects are achieved by this invention based on our discovery that N-acyl-S-haloalkyl, and S-halovinyl, thiolcarbamates as defined herein are not only highly active in fighting infections of plants by the different orders of fungi but also in preventing such infections.

The fungicides of the invention have the general formula

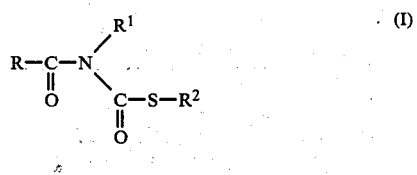

wherein
R = phenyl optionally substituted by halogen atoms, benzyl, a $C_1$-$C_5$ alkyl optionally substituted by halogen atoms;
$R^1$ = a $C_1$-$C_4$ alkyl, phenyl optionally substituted by $C_1$-$C_3$ alkyl;
$R^2$ = —$CCl_3$; —$CCl_2$—$CCl_2X$; —$CCl$=$CClX$; —$CCl_2Y$ in which X=H, Cl; Y=H, F.

The method of preparing the compounds of formula I, which is an object of this invention, consists in reacting a carboxylic acid (II) or its sodium salt with an imidoyl chloride (III). The reaction proceeds as follows:

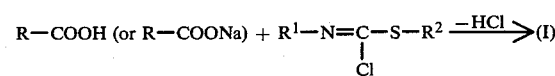

(II)   (III)

(R, $R^1$ and $R^2$ having the same meanings as in general formula I).

The reaction can be conducted in an inert solvent, preferably an aromatic hydrocarbon, for example, benzene, or in a diphase system according to a technique known as "phase transfer".

More particularly, when $R^1$ is a group of alkylic nature the reaction is preferably conducted in a homogeneous phase, in the presence of a tertiary amine, at the solvent boiling temperature. Conversely, when $R^1$ is a group of aromatic nature, the reaction is preferably carried out in phase transfer, using the carboxylic acid in the form of an alkaline salt and, as a solvent mixture, water and an aromatic hydrocarbon, in the presence of small amounts of a quaternary ammonium salt.

The imidoyl chlorides of formula III, such as trichloromethyl thiomidoyl chloride, are generally known compounds and can be prepared by the method described by E. Kuhle [Angew, Chemie, Internat. Ed. 1, No. 12647 (1962)] starting from a nitrogen-substituted formamide according to the following scheme:

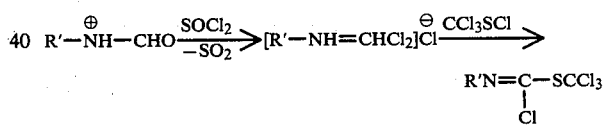

The imidoyl chlorides used in preparing compounds Nos. 1, 3, 8 and 9 described in Examples 1, 2, 3 and 4 below, respectively, and compounds Nos. 2, 4, 5, 6 and 7, which are described in the following Table I, were prepared by the Kuhle method.

TABLE I

Some N-acyl-trichloromethylthiolcarbamates of general formula I, and their physical and chemical characteristics

| No. | Structure | Melting point °C. | S found | S theor. | Cl found | Cl theor. | C found | C theor. | H found | H theor. | N found | N theor. |
|---|---|---|---|---|---|---|---|---|---|---|---|---|
| 2 | $C_6H_5$—C(=O)—N($C_4H_9{}^n$)—C(=O)—$SCCl_3$ | Liquid | 8.98 | 9.04 | 28.63 | 30.0 | | | | | | |
| 4 | $C_6H_5$—C(=O)—N(2-methylphenyl)—C(=O)—$SCCl_3$ | Liquid | 7.25 | 8.25 | 26.9 | 27.4 | 48.35 | 49.5 | 3.38 | 3.11 | 3.31 | 3.60 |

TABLE I-continued

Some N-acyl-trichloromethylthiolcarbamates of general formula I, and their physical and chemical characteristics

| No. | Structure | Melting point °C. | S found | S theor. | Cl found | Cl theor. | C found | C theor. | H found | H theor. | N found | N theor. |
|---|---|---|---|---|---|---|---|---|---|---|---|---|
| 5 | 4—Cl—C$_6$H$_4$—C(=O)—N(—2-CH$_3$-C$_6$H$_4$)—C(=O)—S—CCl$_3$ | 96–97 | 7.50 | 7.58 | 31.90 | 33.53 | | | | | | |
| 6 | Cl—CH$_2$—C(=O)—N(—C$_6$H$_5$)—C(=O)—SCCl$_3$ | 127–130 | | | 39.0 | 40.87 | | | | | | |
| 7 | C$_6$H$_5$—CH$_2$—C(=O)—N(—C$_6$H$_5$)—C(=O)—S—CCl$_3$ | 104–106 | 8.44 | 8.25 | 25.22 | 27.38 | | | | | | |

The compounds of general formula I are endowed with an intense fungicide activity, which is particularly effective in the prevention of infections due to Peronospora (*Plasmopara viticola*), to grey mildew (*Botrytis cinerea*), to bean rust (*Uromyces appendiculatus*). That is, said compounds are capable of hindering the inception of the infection.

The activity of these compounds is similar to that of the compounds widely used in commerce and belonging to classes different from those of the compounds of formula I.

The activities exerted by a number of compounds of this invention in preventing the infections due to Peronospora, grey mildew and bean rust, determined by the method described in Example 5 below, are reported in the following tables.

TABLE II

Preventive activity against vine mildew (Peronospora) by application on the leaves

| Compound No. | R | R$^1$ | R$^2$ | Dose % | Days elapsed between application and infection 1 | 7 |
|---|---|---|---|---|---|---|
| 1 | C$_6$H$_5$ | CH$_3$ | SCCl$_3$ | 0.5 | 100 | 100 |
| | | | | 0.12 | 100 | 100 |
| 2 | C$_6$H$_5$ | n-C$_4$H$_9$ | SCCl$_3$ | 0.5 | 100 | 82 |
| | | | | 0.12 | 100 | 40 |
| 3 | C$_6$H$_5$ | C$_6$H$_5$ | SCCl$_3$ | 0.5 | 100 | 100 |
| | | | | 0.12 | 100 | 100 |
| 4 | C$_6$H$_5$ | 2-CH$_3$—C$_6$H$_4$ | SCCl$_3$ | 0.5 | 100 | 100 |
| | | | | 0.12 | 100 | 80 |
| 5 | 4-Cl—C$_6$H$_4$ | 2-CH$_3$—C$_6$H$_4$ | SCCl$_3$ | 0.5 | 100 | — |
| | | | | 0.12 | 60 | — |
| 6 | CH$_2$Cl | C$_6$H$_5$ | SCCl$_3$ | 0.5 | 100 | 100 |
| | | | | 0.12 | 100 | 100 |
| 8 | C$_6$H$_5$ | C$_6$H$_5$ | CCl$_2$F | 0.5 | 100 | 100 |
| | | | | 0.12 | 100 | 100 |
| 9 | C$_6$H$_5$ | C$_6$H$_5$ | CHCl$_2$ | 0.5 | 100 | 100 |
| | | | | 0.12 | 100 | 100 |

TABLE III

Preventive activity against Botrytis c.(grey mold) by application on leaves of vine plants

| Compound No. | Dose % | Days elapsed from the application to the infection 1 | 7 |
|---|---|---|---|
| | 0.5 | 100 | 100 |
| | 0.37 | 100 | 100 |
| | 0.18 | 100 | 100 |
| 2 | 0.5 | 100 | 90 |
| | 0.18 | 70 | 44 |
| 3 | 0.5 | 100 | 100 |
| | 0.37 | 100 | 100 |
| | 0.18 | 100 | 96 |
| 4 | 0.5 | 100 | 84 |
| | 0.18 | 100 | 78 |
| 5 | 0.5 | 100 | 78 |
| | 0.18 | 100 | 64 |
| 6 | 0.5 | 100 | 100 |
| | 0.37 | 100 | 100 |
| | 0.18 | 100 | 80 |

TABLE IV

Preventive activity against bean rust by application on the plant leaves

| Compound No. | Dose % | Days elapsed from the application to the infection 1 | 6 |
|---|---|---|---|
| 1 | 1 | 100 | 100 |
| | 0.5 | 100 | 100 |
| 2 | 1 | 100 | 100 |
| | 0.5 | 99 | 66 |
| 4 | 1 | 100 | 100 |
| | 0.5 | 95 | 95 |
| 8 | 1 | 100 | 100 |
| | 0.5 | 100 | 100 |
| 9 | 1 | 100 | 100 |
| | 0.5 | 100 | 100 |

TABLE V

Preventive activity against Botrytis cinerea (grey mildew) by application on tomato plant leaves

| Compound No. | Dose % | Preventive Acitivty After 1 day (1) | After 7 days (1) |
|---|---|---|---|
| 8 (See Ex. 4) | 0.5 | 100 | 100 |
| | 0.37 | 100 | 100 |
| | 0.18 | 100 | 100 |
| 9 (See Ex. 5) | 0.5 | 84 | |
| | 0.18 | 70 | |

(1) Days elapsed from the application to the infection.

The compounds of the present invention can be formulated according to conventional methods in the form of powders, wettable powders, suspensions, emulsions, solutions in solvents, by making use, if necessary, of surfactants.

The following examples are given to illustrate the invention in more detail and are not intended to be limiting.

EXAMPLE 1

Preparation of compound No. 1:

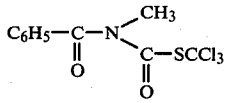

A mixture of 3.6 g of benzoic acid and of 6.7 g of methylimino-chloro-S-trichloromethyl-thioformate

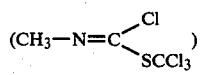

in 50 ml of benzene was additioned, at room temperature, to 4.8 ml of triethylamine in 20 ml of benzene. The reaction mixture was refluxed for 3 hours. The triethylamine chlorohydrate was then separated and the organic phase was passed over a 4 cm thick silica gel layer. After evaporation of the solvent, 10 g of raw product were obtained which, after treatment with 20 ml of n-hexane, precipitated 2.5 g of a yellow solid.

This solid was crystallized from 95% ethanol (15 ml) and yielded 1.5 g of compound No. 1 as a white crystalline solid having a melting point equal to 126°-127° C.

Elemental analysis:
S found=9.98%;
S theor.=10.31%; Cl found=32.42%;
Cl theor.=34.2%.

I.R. analysis:
1695 cm$^{-1}$ ($\delta$C=O),
1650 cm$^{-1}$ ($\delta$C=O), other bands at: 1210 cm$^{-1}$, 1060$^{-1}$, 795 cm$^{-1}$.

N.M.R. analysis:
3.34 ppm (S, 3H),
7.56 ppm (S, 5H).

EXAMPLE 2

Preparation of compound No. 3:

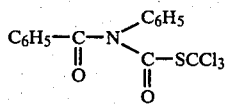

29 g of phenylimino-chloro-S-trichloromethyl-thioformate

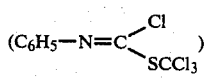

dissolved in 100 ml of benzene; 29 g of sodium benzoate, dissolved in 40 ml of H$_2$O; 3.6 g of N-acetyl-N,N,N-trimethylammonium bromide were introduced into a 500-ml flask equipped with a mechanical stirrer. It was heated at reflux for 3 hours under intense stirring, then it was cooled and, after addition of 50 ml of diethyl ether, two phases were separated.

The organic phase was dried and evaporated to yield a semisolid residue (36.2 g), which was diluted with 20 ml of diethyl ether and 20 ml of n-hexane: from this mixture 20 g of raw product was precipitated. By crystallization of this product from 95% ethanol (70 ml) it was possible to obtain 16 g of compound No. 3, having a melting point of 102°-103° C.

Elemental analysis:
S found=8.47%;
S theor.=8.56%; Cl found=29.96%;
Cl theor.=28.4%.

I.R. analysis:
1680 cm$^{-1}$ ($\delta$C=O),
1660 cm$^{-1}$ ($\delta$C=O), other bands at 1320 cm$^{-1}$, 1250 cm$^{-1}$, 790 cm$^{-1}$.

N.M.R. analysis:
7.35 ppm (m=multiplet).

EXAMPLE 3

Preparation of compound No. 8: N-benzoyl-N-phenyl-S-dichlorofluoromethyl-thiolcarbamate

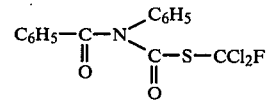

2.7 g of N-phenyl-S-dichlorofluoromethyl-thioimidoyl chloride:

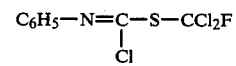

[prepared as described in Angew. Chemie Int. Ed. 1/12, 647 (1962)]
20 ml of toluene,
4.5 g of sodium benzoate,
0.3 g of cetyl-trimethylammonium bromide, and
10 ml of water
were introduced into a 100-ml flask equipped with a stirrer, a thermometer and a reflux condenser.

The reaction mixture was heated under intense stirring at 70°-75° C. for 2 hours. After cooling, 20 ml of diethylether and 20 ml of water were added.

The organic phase separated, anhydrified with anhydrous Na$_2$SO$_4$, and the solvent was then evaporated at reduced pressure. 3.1 g of an oil were obtained, to which 5 ml of n-hexane were added. The solution was cooled down to $-10°$ C. A solid was obtained which was recrystallized from 95% ethanol (melting point=84.5°-85.5° C.).

Elemental analysis:
F: found=5.07%;
theoretical=5.31%;
Cl: found=19.56%;
theoretical=19.80%;
S: found=8.83%;
theoretical=8.95%.

I.R. analysis:
consistent with the attributed structure;
significant bands at 1680 and 1645 cm$^{-1}$.

EXAMPLE 4

Preparation of compound No. 9: N-benzoyl-N-phenyl-S-dichloromethyl-thiolcarbamate

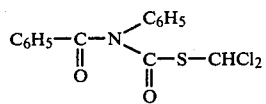

Starting from sodium benzoate and N-phenyl-S-dichloromethyl-thioimidoyl chloride and operating according to the procedure described in Example 3, the above-mentioned thiolcarbamate was prepared, which exhibited the following characteristics: melting point=110°–111° C. (crystallized from 95% ethanol)
Elemental analysis:
Cl: found=20.72%; theoretical=20.85%;
S: found=9.93%; theoretical=9.43%.
I.R. analysis:
consistent with the attributed structure; significant bands at 1660 and 1685 cm$^{-1}$
N.M.R. analysis:
(CDCl$_3$, TMS) (ppm) 7.03 (s, 1H) 7.35 (m, 10H), (s=singlet, m=multiplet).

EXAMPLE 5

Method of determining the fungicide activity (a) PREVENTIVE ACTIVITY ON VINE MILDEW (Plasmopara viticola (B. et Col.) Berl. et de Toni).

Leaves of vine plants cv. Dolcetto, grown in pots in a conditioned chamber at 25° C. and 60% of relative humidity, were treated by sprinkling both leaf faces with a hydroacetone solution at 20% of acetone (vol.-/vol.) of the product under examination.

After one day, half of the plants under test were artificially infected with an aqueous suspension of Plasmopara viticola conidia (200,000 conidia/cc). After a 24-hour dwelling time in a humidity-saturated chamber at 21° C., the plants were transferred into a chamber having a relative humidity of 70% and a temperature of 21° C. for an incubation period of 7 days.

The other half of the plants were artificially infected after 7 days by inoculating the lower faces of the leaves in the same manner as those infected after 24 hours. The infection degree was evaluated visually (by sight), at the conclusion of the incubation period, on the basis of a measuring scale ranging from 100 (healthy plants) to 0 (completely infected plants).

(b) PREVENTIVE ACTIVITY AGAINST BOTRYTIS CINEREA ON TOMATO PLANTS.

The activity was evaluated on tomato plants cv. Marmande, 40 days old, grown in pots in a conditioned chamber at 25° C. and 60% of relative humidity.

Both faces of the leaves of the plants were sprinkled with a hydroacetone solution at 20% of acetone (vol.-/vol.) of the product under test. One half of the test plants were artificially infected, after one day, by inoculating both faces of each leaf with a suspension in a carrot broth of Botrytis cinerea (1,000,000 of spores/cc). After a 24-hour dwelling time in a humidity-saturated chamber at 26° C., the plants were transferred into a chamber having a relative humidity of 70% and a temperature of 26° C. for an incubation period of 6 days.

The other half of the test plants was artificially infected after 7 days by inoculating both faces of the leaves in the same manner as those infected after 24 hours.

The infection degree was evaluated visually, at the conclusion of the incubation period, on the basis of an evaluation scale ranging from 100 (healthy plants) to 0 (fully infected plants).

(c) PREVENTIVE ACTIVITY ON BEAN RUST [Uromyces appendiculatus (Pers.) Link].

The leaves of bean plants cv. Borlotto of Vigevano, grown in pots in a conditioned chamber at 25° C. and 60% of relative humidity, were treated by sprinkling both leaf faces with a hydroacetone solution at 20% of acetone (vol./vol.) of the product under test.

One half of the test plants were artificially infected, after 24 hours, by inoculating the lower face of each leaf with a suspension of Uromyces appendiculatus (200,000 spores/cc). After a 24-hour dwelling time in a humidity-saturated chamber at 21° C., the plants were transferred to a chamber at 70% of relative humidity and 23° C. for the incubation period (14 days).

The other half of the test plants was artificially infected after 7 days by inoculating the lower faces of their leaves in the same manner as those infected after 24 hours.

The infection degree was evaluated visually, at the conclusion of the incubation period, on the basis of an evaluation scale ranging from 100 (healthy plants) to 0 (completely infected plants).

What we claim is:

1. Compounds of general formula:

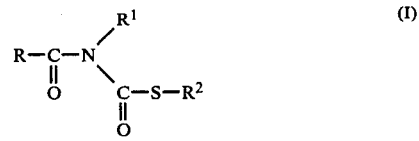

wherein:
R=phenyl, phenyl substituted by halogen atoms, benzyl, C$_1$–C$_5$ alkyl, or a C$_1$–C$_5$ alkyl substituted by halogen atoms;
R$^1$=C$_1$–C$_4$ alkyl, phenyl, or phenyl substituted by C$_1$–C$_3$ alkyls;
R$^2$=—CCl$_3$; —CCl$_2$—CCl$_2$X, —CCl=CClX or —CCl$_2$Y, in which X=H, Cl; Y=H, F.

2. Compounds according to claim 1, in which R$^2$ is C—Cl$_3$.

3. Compounds according to claim 1, in which R$^2$ is CHCl$_2$.

4. Compounds according to claim 1, in which R$^2$ is C—Cl$_2$—F.

5. A compound according to claim 4, and which is N-benzoyl-N-phenyl-S-dichlorofluoromethyl-thiolcarbamate of formula:

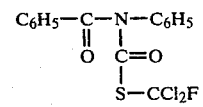

6. A compound according to claim 3, and which is N-benzoyl-N-phenyl-S-dichloromethyl-thiolcarbamate of formula:

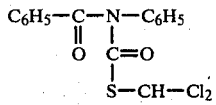

7. A compound according to claim 1, and which is benzoyl-N-(methyl)-N-(trichloromethyl-thiol)-carbamate.

8. A compound according to claim 1, and which is benzoyl-N-(n.butyl)-N-(trichloromethyl-thiol)-carbamate.

9. A compound according to claim 1, and which is benzoyl-N-(phenyl)-N-(trichloromethyl-thiol)-carbamate.

10. A compound according to claim 1, and which is benzoyl-N-(2-toluyl)-N-(trichloromethyl-thiol)-carbamate.

11. A compound according to claim 1, and which is 4-chlorobenzoyl-N-(2-tolyl)-N-(trichloromethylthiol)-carbamate.

12. A compound according to claim 1, and which is chloroacetyl-N-(phenyl)-N-(trichloromethyl-thiol)-carbamate.

13. A process for preparing the compounds of claim 1, characterized in that a carboxylic acid or the sodium salt thereof is reacted with an imidoyl chloride according to the equation:

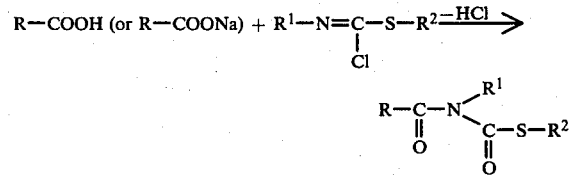

in which R, $R^1$ and $R^2$ have the meanings as in claim 1.

14. The process of claim 13, in which the reaction between the carboxylic acid and imidoyl chloride is effected in an aromatic solvent, in the presence of a tertiary amide and at the boiling temperature of the solvent.

15. The process of claim 13, in which the reaction between the sodium salt of the carboxylic acid and imidoyl chloride is effected in an aromatic hydrocarbon and water as solvents used in the presence of a quaternary ammonium salt.

16. A method of fighting fungi infections of useful plants by fungi of the different orders Ficomicoeti, Ascomicoeti and Basimiomicoeti, characterized in that, before the inception of the infection, an effective amount of at least one of the compounds of claim 1 is distributed, as such or in the form of an agrarian formulation, on the plants in a dose of at least 0.12%.

17. The method of claim 16, characterized in that the infection to be fought is due to fungi belonging to the order of Ficomicoeti.

18. The method of claim 16, characterized in that the infection to be fought is due to fungi belonging to the order of Ascomicoeti.

19. The method of claim 16, characterized in that the infection to be fought is due to fungi belonging to the order of Basidiomicoeti.

20. Fungicide compositions the active constituent of which is at least one of the compounds of claim 1, in an effective amount of at least 0.12% and containing a suitable carrier.

21. The method of claim 16, further characterized in that the infection to be fought is due to Botrytis cinerea.

22. The method of claim 16, further characterized in that the infection to be fought is due to Plasmopora viticola.

23. The method of claim 16, further characterized in that the infection to be fought is due to Uromyces appendiculatus.

* * * * *

UNITED STATES PATENT AND TRADEMARK OFFICE
CERTIFICATE OF CORRECTION

PATENT NO. : 4,301,174
DATED : Nov. 17, 1981
INVENTOR(S) : Ottorino PALLA; Remo GALLI; Franco GOZZO and Simone LORUSSO It is certified that error appears in the above—identified patent and that said Letters Patent is hereby corrected as shown below:

Cols. 3 and 4, Tables II, III, IV, and V, in the sub-heading of each of said Tables, "Dose %" should be ---Dose $\%_o$---.

Signed and Sealed this

Ninth Day of March 1982

[SEAL]

Attest:

GERALD J. MOSSINGHOFF

Attesting Officer — Commissioner of Patents and Trademarks